United States Patent
Cui et al.

(10) Patent No.: US 11,623,938 B2
(45) Date of Patent: Apr. 11, 2023

(54) LIVER-TARGETING COMPOUND HAVING THYROID HORMONE RECEPTOR AGONIST CHARACTERISTICS AND PHARMACEUTICAL COMPOSITION THEREOF

(71) Applicant: KYLONOVA (XIAMEN) BIOPHARMA CO., LTD., Fujian (CN)

(72) Inventors: Kunyuan Cui, Fujian (CN); Shengjun Wang, Fujian (CN); Yanchun Du, Fujian (CN)

(73) Assignee: KYLONOVA (XIAMEN) BIOPHARMA CO., LTD., Xiamen (CN)

( * ) Notice: Subject to any disclaimer, the term of this patent is extended or adjusted under 35 U.S.C. 154(b) by 0 days.

(21) Appl. No.: 17/790,191

(22) PCT Filed: Sep. 2, 2020

(86) PCT No.: PCT/CN2020/112941
§ 371 (c)(1),
(2) Date: Jun. 30, 2022

(87) PCT Pub. No.: WO2021/135335
PCT Pub. Date: Jul. 8, 2021

(65) Prior Publication Data
US 2023/0065479 A1    Mar. 2, 2023

(30) Foreign Application Priority Data
Dec. 31, 2019    (CN) .......................... 201911407857.4

(51) Int. Cl.
C07H 15/18    (2006.01)
A61P 1/16    (2006.01)
C07H 1/00    (2006.01)

(52) U.S. Cl.
CPC ................ *C07H 15/18* (2013.01); *A61P 1/16* (2018.01); *C07H 1/00* (2013.01)

(58) Field of Classification Search
None
See application file for complete search history.

(56) References Cited

FOREIGN PATENT DOCUMENTS

| CN | 109331185 A | 2/2013 |
| CN | 107929273 A | 4/2018 |
| CN | 109331185 A | 2/2019 |
| CN | 111116684 A | 5/2020 |
| WO | 9857919 A1 | 12/1998 |

OTHER PUBLICATIONS

First Search of China Patent Application CN201911407857.4, dated Jul. 14, 2020.
Notification to Grant Patent Right for Invention 201911407857.4 dated Aug. 27, 2020.
International Search Report of Application No. PCT/CN2020/112941 dated Dec. 23, 2020.
Written Opinion of Application No. PCT/CN2020/112941 dated Dec. 23, 2020.
Huang Yuanyu st al., "Desialic Acid Glycoprotein Receptor and Its Application in Hepatic Targeted Delivery of Drugs", Advances in Biochemistry and Biophysics, vol. 42, No. 6, Dec. 31, 2015 (Dec. 31, 2015), pp. 501-510.
June Rae Merwin et al.. "Targeted Delivery of DNA Using YEE(GaINAcAH>3, a Synthetic Glycopeptide Ligand for the Asialoglycoprotein Receptor", Bioconjugate Chem., vol. 5, No. 6, Dec. 1994. 31 (Dec. 31, 1994), pp. 612-620.

*Primary Examiner* — Layla D Berry
(74) *Attorney, Agent, or Firm* — Ladas & Parry LLP (57) ABSTRACT

The present invention belongs to the field of biomedicine, specifically relates to the field of targeting medicine. More specifically, the present invention relates to a liver-targeting compound having thyroid hormone receptor agonist characteristics and a pharmaceutical composition thereof. The compound is a compound represented by formula (1). The compound can be used for treating and/or preventing diseases caused by thyroid hormone dysregulation, and can also effectively reduce lipids in plasma and liver cells.

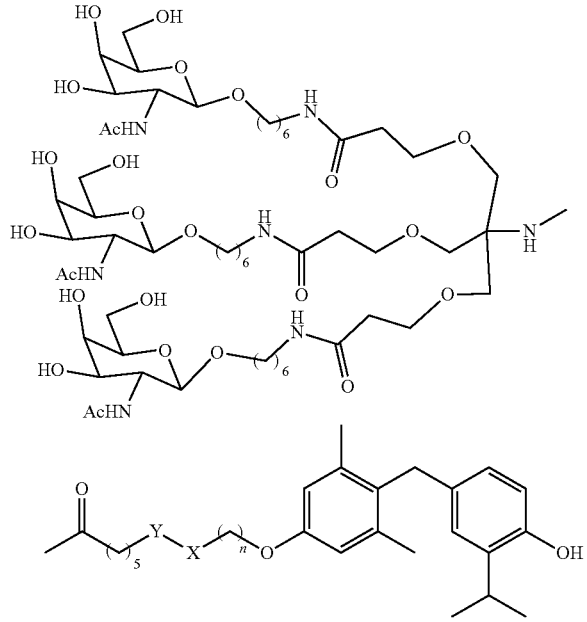

formula (1)

13 Claims, 9 Drawing Sheets

LIVER-TARGETING COMPOUND HAVING THYROID HORMONE RECEPTOR AGONIST CHARACTERISTICS AND PHARMACEUTICAL COMPOSITION THEREOF

CROSS-REFERENCE TO RELATED APPLICATIONS

This application is a national stage entry of International Patent Application No. PCT/CN2020/112941 filed on 2 Sep. 2020, which claims priority to Chinese Patent Application No. 201911407857.4 filed on 31 Dec. 2019. The aforementioned patent applications are hereby incorporated by reference in their entirety.

TECHNICAL FIELD

The present invention belongs to the field of biomedicine, and specifically relates to the field of targeted drugs. More specifically, the present invention relates to a liver-targeting compound with the characteristics of thyroid hormone receptor agonist, and a pharmaceutical composition thereof.

BACKGROUND ART

Non-alcoholic fatty liver disease (NAFLD), as a chronic liver disease, is characterized by excessive accumulation of lipids, mainly excessive accumulation of triglycerides (TG), in hepatocytes. The pathological process of NAFLD includes a series of pathological changes in the liver, starting from simple triglyceride accumulation in hepatocytes (hepatic steatosis) to inflammatory and hepatocyte balloon injury developing into non-alcoholic steatohepatitis (NASH), and eventually leading to liver fibrosis and cirrhosis. It is still unclear about the exact mechanism of the transition from steatosis to steatohepatitis. There is a double-hit hypothesis: the first hit involves the accumulation of TG in hepatocytes, leading to a vicious circle of metabolic dysfunction. Once the presence of liver steatosis is identified, the progression to steatohepatitis involves the second hit where oxidative stress plays a key role. NAFLD/NASH is currently a chronic liver disease being worldly more and more common and the patients tends to be younger. Public information shows that the global incidence of NAFLD is 15% to 30%, of which 10% to 20% will develop into NASH. Incomplete statistics showed that the NAFLD population was about 240 million in China in 2016, and it was estimated that the NAFLD population would increase to about 310 million by 2030, including about 2.3 million patients with liver cirrhosis. In the United States, NASH had become the second primary cause of liver transplantation after chronic hepatitis C, and was expected to surpass chronic hepatitis C in 2020 and become the primary cause of liver transplantation in the United States, as pointed in a 2017 article in the journal of Nature. Such situation is mainly due to lack of a currently recognized pharmacological treatment for NASH and lack of attention to such diseases. So far, NASH has main known pathogenic factors including metabolic syndromes such as obesity, type 2 diabetes, hyperlipidemia, and hypertension. No therapeutic drug for this indication has been approved for marketing in the world. The current methods of treatment and intervention are mainly based on lifestyle changes, including diet and exercise, but the effect is not obvious.

Thyroid hormones T4 and T3 have various functions and are effective substances for regulating glucose and lipid metabolism and body weight, and in particular, they play an important role in hepatic lipid homeostasis. They exert physiological effects by binding to their specific nuclear receptors, thyroid hormone receptors TR-α and TR-β, and have an impact by interacting with the specific hormone receptors TR-α and TR-β that are widely distributed throughout the body. TR-β is mainly expressed in the liver and has an important effect on lipid metabolism, including reducing low-density lipoprotein (LDL) cholesterol and triglycerides and lowering systemic obesity and body weight (Pramfalk C, et al., Biochim Biophys Acta 1812:929-937), and can reduce the lipid content by improving the lipid metabolism rate in the liver. A study by Pena A et al. showed that T3 can inhibit hepatocyte steatosis and repair steatotic hepatocytes (Perra A et al., FASEB J 22:2981-2989). However, excessive thyroid hormone is prone to side effects including adverse reactions of thyroid-stimulating hormone (TSH), heart, bone and muscle (Braverman L E, et al., editors. Lippincott: The Thyroid 2000: 515-517) and damage to liver function resulting in elevated liver enzymes such as ALT, AST and GGT. TSH is a hormone secreted by the adenohypophysis. The thyroid-stimulating hormone secretion of adenohypophysis is, on one aspect, promoted by the thyroid-stimulating hormone releasing hormone (TRH) secreted by hypothalamus, and on the other aspect, inhibited by thyroid hormone feedback. The two aspects antagonize each other, and they form hypothalamus-adenohypophysis-thyroid axis.

TSH is mainly responsible for regulating the proliferation of thyroid cells, blood supply of the thyroid, and the synthesis and secretion of thyroid hormones, and plays the most important regulatory role in maintaining normal thyroid function. Diseases in adenohypophysis itself can directly affect the synthesis and release of TSH. When the thyroid itself causes abnormal thyroid hormone synthesis and secretion, it can also affect the secretion of TSH in adenohypophysis and TSH level in serum. Similarly, when hypothalamic disease affects the secretion of TRH, it also affects the secretion of TSH in adenohypophysis and the TSH level in serum.

The main function of TSH is to control the thyroid. It can promote the synthesis of thyroid hormones, and the release of the generated thyroid hormones into the blood. It also plays an important role in the growth and metabolism of the thyroid itself. Exogenous thyroid hormone entering the body can cause thyroid-stimulating hormone to have an inhibitory effect similar to thyroid hormone feedback, thereby affecting the normal secretion of thyroid-stimulating hormone, which is prone to cause hyperthyroidism, accelerated heart rate or reduced TSH. Clinically, if a drug accelerates the heart rate by 15% and reduces TSH by 30%, it indicates that the drug has side effects on the heart and thyroid. A study in Literature has shown that T3 has the ratios of $ED_{15}$ which triggers 15% increase in heart rate and $ED_{30}$ which inhibits TSH by 30% to $ED_{50}$ which reduces high cholesterol (TC) of 1.5 and 0.4 respectively (GARY J et al., Endocrinology 145(4): 1656-1661), and therefore, exogenous thyroid hormone is not suitable as drugs for clinical regulation of lipid metabolism or NASH treatment, although it shows good effects of reducing lipids and inhibiting hepatocyte steatosis. Due to these adverse effects, thyroid hormones are limited in its further application in lipid metabolism and NASH treatment. If the side effects of thyroid hormones on the thyroid axis, heart and other organs can be eliminated or reduced, predictable therapeutic effects can be obtained.

Thyroid hormone β receptor agonists are a class of new compounds or their precursors modified based on the structure of the thyroid hormone T3. Thyroid hormones regulate the differentiation, development and metabolic balance in the body by binding to the thyroid hormone receptors TR-α and TR-β in various tissues. Thyroid hormone β receptor agonists can selectively act on the subtype TR-β1 of TR-β1, and has affinity and selectivity for TR-β1 much greater than those for TR-α. TR-β1, which exists in most tissues, especially the liver and is less distributed in the heart, mediates the effect of thyroid hormones in the liver and adipose tissue. The new compounds or their precursors modified based on the structure of the thyroid hormone T3 maintain the above effects of thyroid hormone with less side effects in TR-α and on liver function, and thus are currently an important development field of new drugs for treatment of non-alcoholic fatty liver disease (NAFLD).

In order to reduce the side effects of the drug for treating NAFLD or NASH, there is an urgent need to develop a new drug in the field of biomedicine, which can maintain the lipid metabolism of thyroid hormones in the liver without causing the corresponding side effects in other tissues.

SUMMARY OF THE INVENTION

An object of the present invention is to provide a liver-targeting compound with the characteristics of thyroid hormone receptor agonist.

Another object of the present invention is to provide a method for preparing the liver-targeting compound with the characteristics of thyroid hormone receptor agonist.

Yet another object of the present invention is to provide a use of the liver-targeting compound with the characteristics of thyroid hormone receptor agonist.

Still another object of the present invention is to provide a pharmaceutical composition comprising the liver-targeting compound with the characteristics of thyroid hormone receptor agonist.

In order to achieve the above objects, in one aspect, the present invention provides a liver-targeting compound with the characteristics of thyroid hormone receptor agonist represented by formula (1):

formula (1)

wherein, n is an integer of 1 to 10, preferably an integer of 1 to 3; X is carbonyl; Y is NH or an oxygen atom.

In one embodiment of the present invention, the compound represented by formula (1) is preferably compound GBL-0603:

GBL-0603

Exogenous thyroid hormones entering the body will be distributed throughout the body, resulting in side effects on the thyroid axis, heart, muscle, bone and liver function.

N-acetylgalactosamine has a high affinity for the asialoglycoprotein receptor (ASGPR, a receptor specifically expressed by hepatocytes) in the liver, which can make a compound with a structure comprising galactosamine have active liver-targeting, and can make thyroid hormone β receptor agonists have active liver-targeting on the basis of its high affinity and selectivity on TR-β1, further decrease its distribution in other tissues and reduce its side effects.

The liver-targeting compound with the characteristics of thyroid hormone receptor agonist provided by the present invention comprises three galactosamine moieties at the left end and a T3-like moiety at the right end, which are connected by esterification or amidation, such that the whole compound not only has the liver-targeting property and maintains the effect of thyroid hormone β receptor agonist, but also minimizes the occurrence of side effects.

In another aspect, the present invention provides a method for preparing the liver-targeting compound with the characteristics of thyroid hormone receptor agonist, comprising a step of forming an ester or amide linkage between compound A and compound B (as an intermediate or a starting material):

wherein, n is an integer of 1 to 10, preferably an integer of 1 to 3; $X_1$ is —COOH; $Y_1$ is an amino group or a hydroxyl group; $X_1$ and $Y_1$ may also be other groups that can form an ester or amide linkage between compound A and compound B.

In still another aspect, the present invention provides a use of the liver-targeting compound with the characteristics of thyroid hormone receptor agonist in preparation of a medicament for treatment and/or prevention of a disease caused by dysregulation of thyroid hormone, wherein the disease includes metabolic disease, preferably includes obesity, hyperlipidemia, hypercholesterolemia, diabetes, non-alcoholic fatty liver disease, non-alcoholic steatohepatitis, alcoholic fatty liver disease, alcoholic steatohepatitis, atherosclerosis, cardiovascular diseases, hypothyroidism, thyroid cancer.

In a preferred embodiment of the present invention, the disease is non-alcoholic fatty liver disease or non-alcoholic steatohepatitis.

In still another aspect, the present invention provides a pharmaceutical composition for treatment and/or prevention of a disease caused by dysregulation of thyroid hormone, comprising a therapeutically effective amount of the above liver-targeting compound with the characteristics of thyroid hormone receptor agonist and optionally, a pharmaceutically acceptable excipient, wherein the pharmaceutically acceptable excipient includes an intestinal absorption enhancer, which includes sodium salts of medium-chain fatty acids, cholates, cyclodextrin and derivatives thereof, cationic polymers, anionic polymers and thiolated polymers.

In an embodiment of the present invention, the sodium salt of medium-chain fatty acid is sodium caprate. Preferably, the weight ratio of the liver-targeting compound with the characteristics of thyroid hormone receptor agonist to sodium caprate is 1:0.2 to 1:0.75.

In a preferred embodiment of the present invention, the dosage form of the pharmaceutical composition is an injection, or an oral rapid or sustained release preparation.

The compound or pharmaceutical composition provided by the present invention can be used clinically in mammals, including humans and animals, and can be administered orally, nasally, transdermally, pulmonarily, or gastrointestinally. Oral administration is the most preferred. The most preferred daily dose is 0.08 to 10 mg/kg body weight and administered once daily, or 0.08 to 5 mg/kg body weight and administered several times a day. No matter what kind of administrating method is used, the optimal dose regimen for an individual should be based on the specific treatment protocol. Generally, starting from a small dose, the dose is gradually increased until an optimal dose is achieved.

In summary, the liver-targeting compound with the characteristics of thyroid hormone receptor agonist provided by the present invention has two advantages: 1) using the high affinity of N-acetylgalactosamine for asialoglycoprotein receptors on the surface of hepatocytes to enhance the targeting to the liver and reduce its distribution in other tissues; 2) using the high affinity of T3 structural analogs for TR-β to further reduce unnecessary side effects. The two of N-acetylgalactosamine and T3 structural analog are combined to form a complete compound, such that it can specifically enter hepatocytes to exert the role of thyroid hormone receptor agonist, regulate lipid metabolism, reverse liver steatosis and inflammation, and slow down liver fibrosis.

Figure 3:
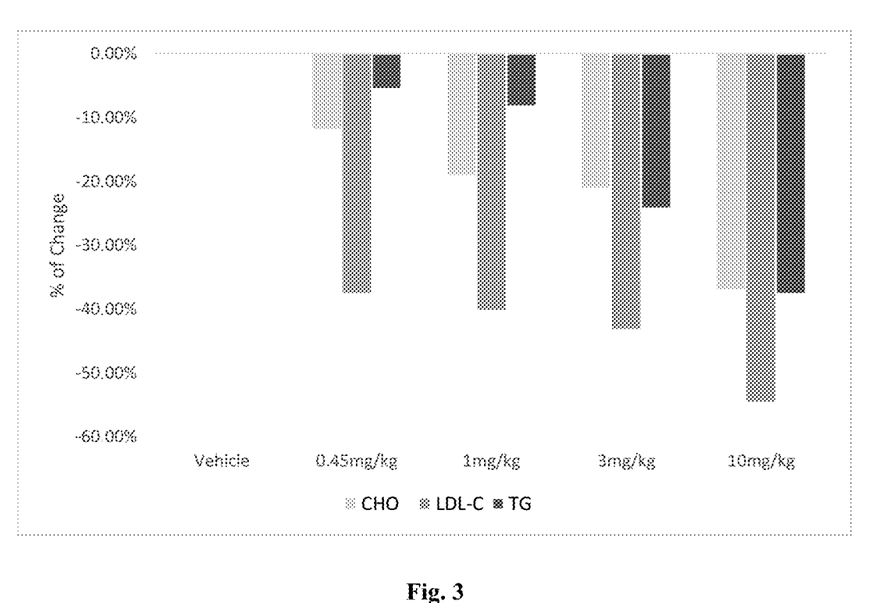
FIG. 3 is a diagram showing the effect of GBL-0603 on reducing CHO, TG and LDL-C in the serum of db/db obese model mice in Example 2.
Figure 4:
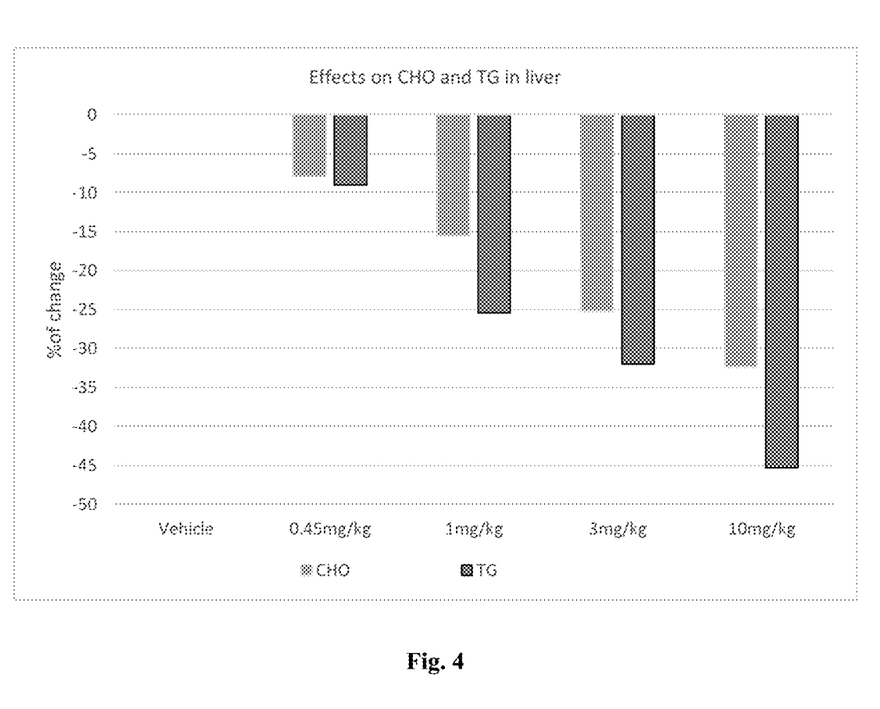
FIG. 4 is a diagram showing the effect of GBL-0603 on reducing CHO and TG in liver tissue cells of db/db obese model mice in Example 2.
Figure 5:
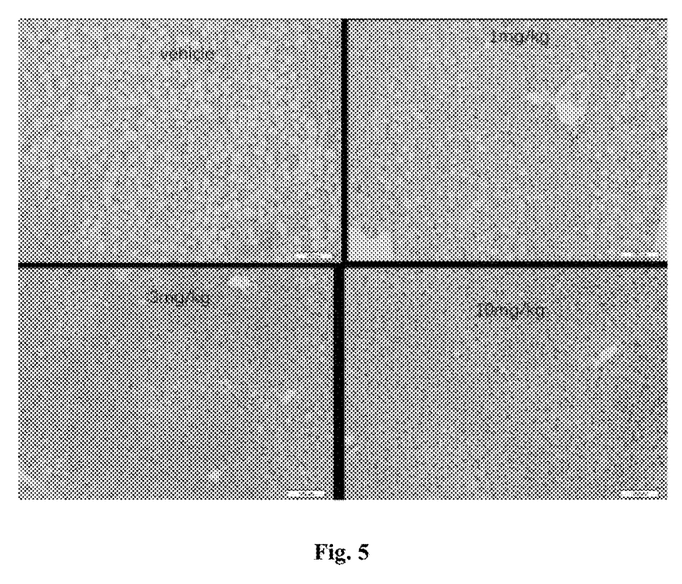
FIG. 5 is illustrative micrographs of liver sections stained with HE in Example 2, showing the effect of GBL-0603 on histopathological change.
Figure 6:
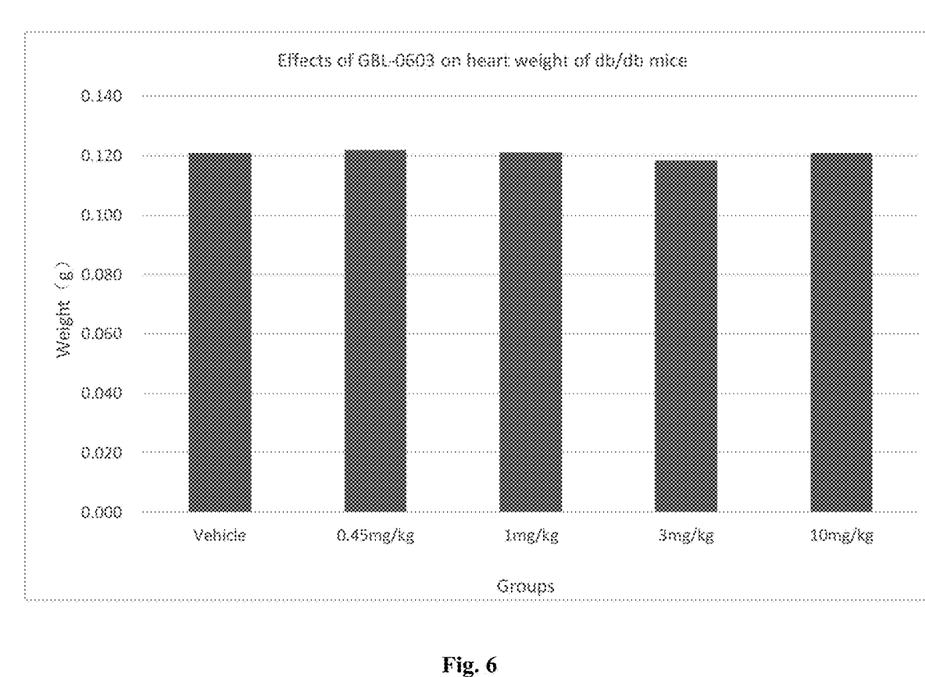
FIG. 6 is a diagram showing the effect of GBL-0603 on the heart weight of db/db obese model mice in Example 2.
Figure 7:
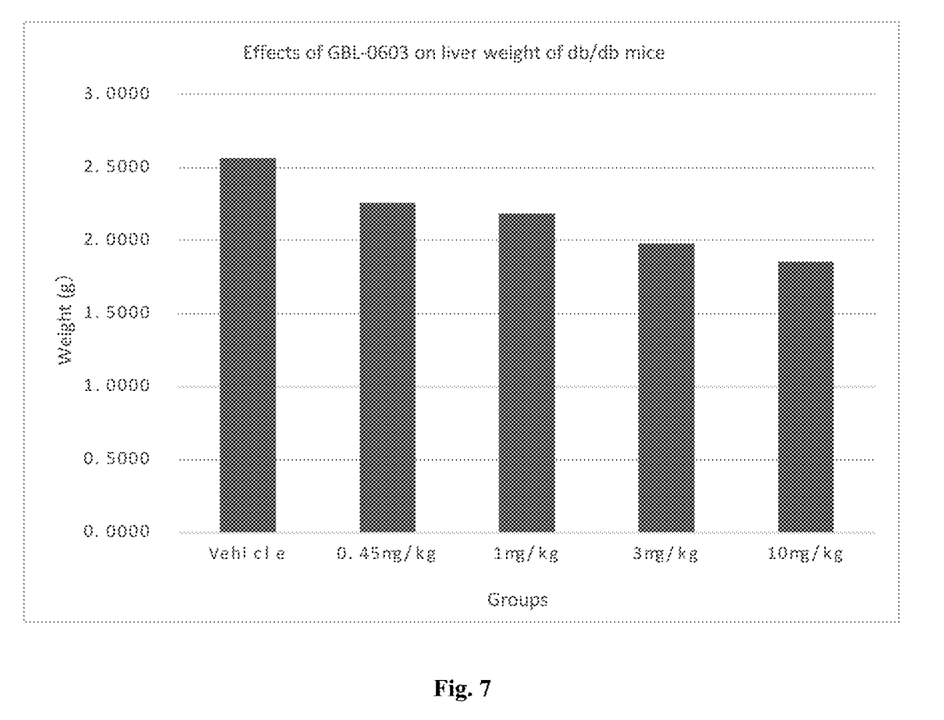
FIG. 7 is a diagram showing the effect of GBL-0603 on the liver weight of db/db obese model mice in Example 2.
Figure 8:
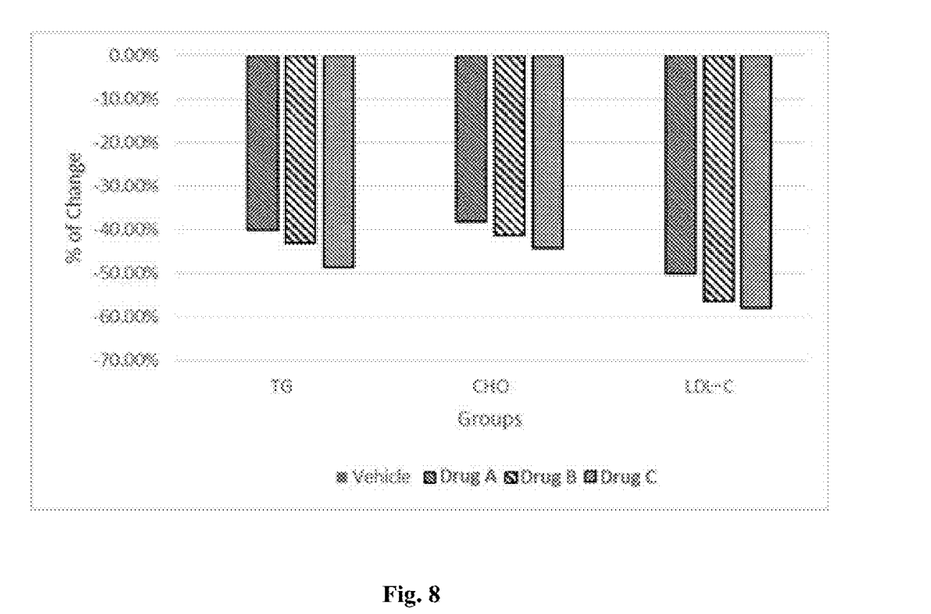
FIG. 8 is a diagram showing the effect of GBL-0603 on CHO, TG and LDL-C in the serum of db/db obese model mice in Example 3.
Figure 9:
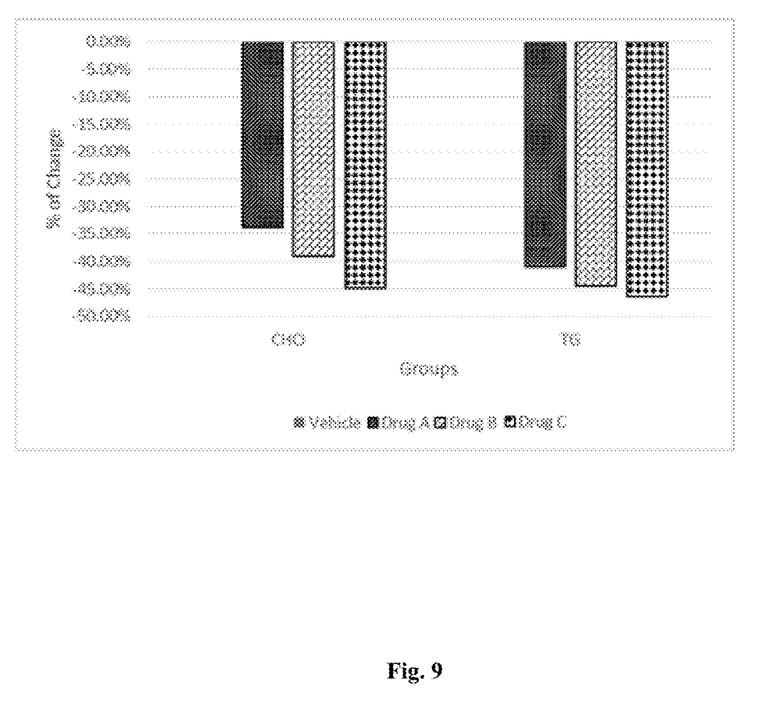
FIG. 9 is a diagram showing the effect of GBL-0603 on CHO and TG in the liver of db/db obese model mice in Example 3.
Figure 10:
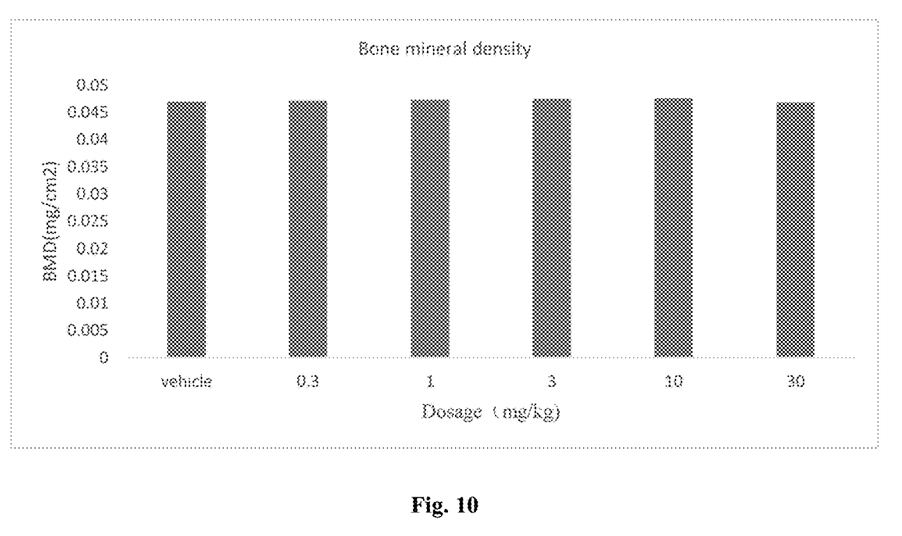
FIG. 10 is a diagram showing the effect of GBL-0603 on the bone mineral density of normal mice in Example 4.
Figure 11:
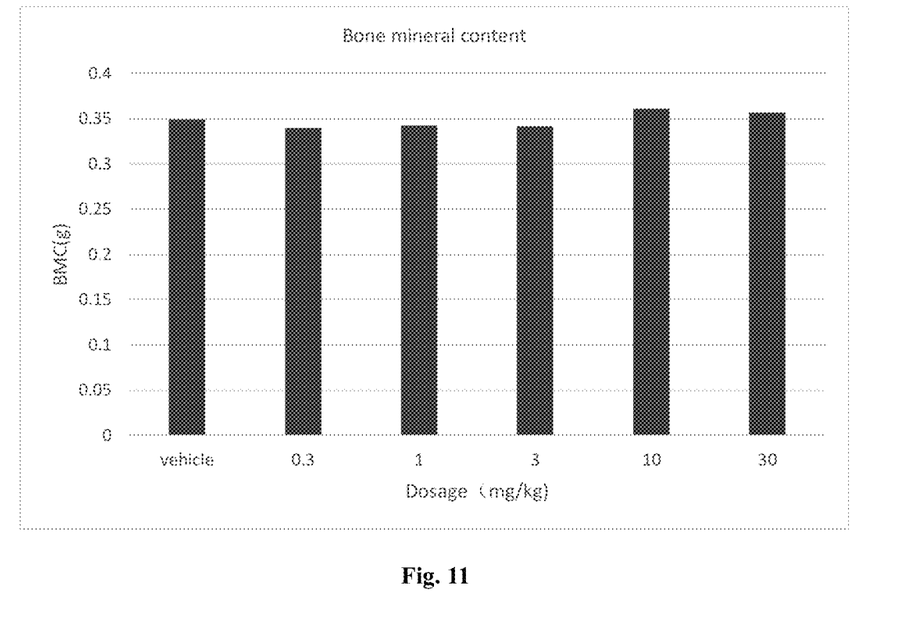
FIG. 11 is a diagram showing the effect of GBL-0603 on the bone mineral content of normal mice in Example 4.
Figure 12:
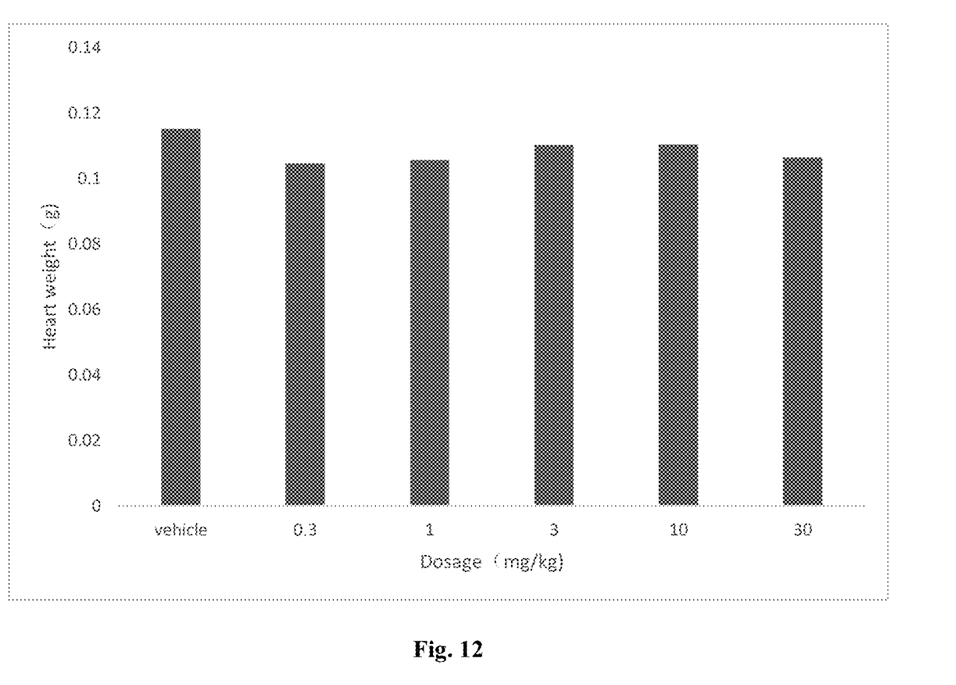
FIG. 12 is a diagram showing the effect of GBL-0603 on the heart weight of normal mice in Example 4.
Figure 13:
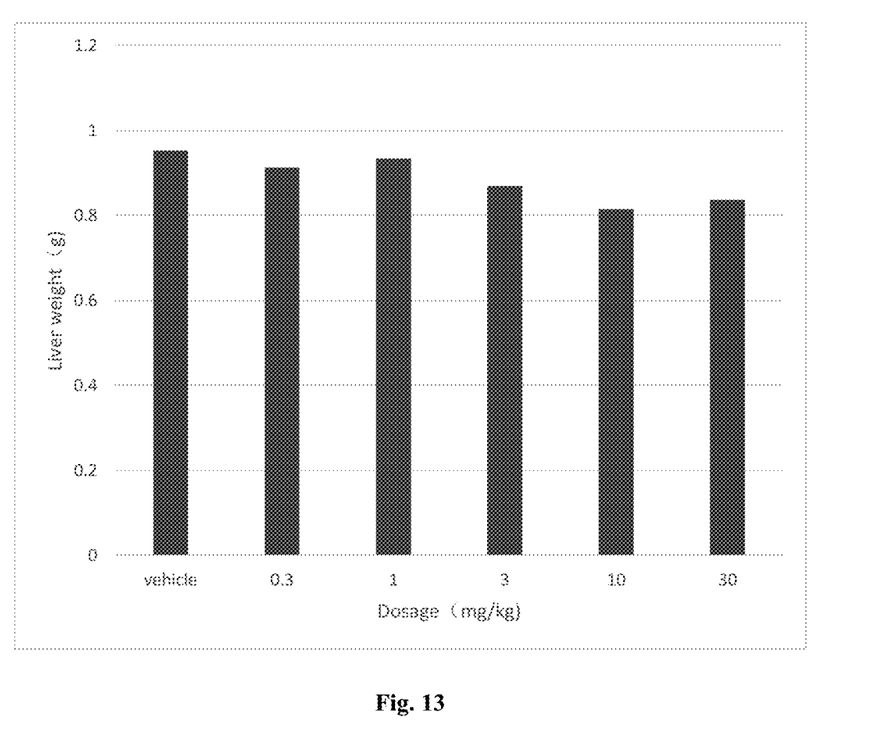
FIG. 13 is a diagram showing the effect of GBL-0603 on the liver weight of normal mice in Example 4.
Figure 14:
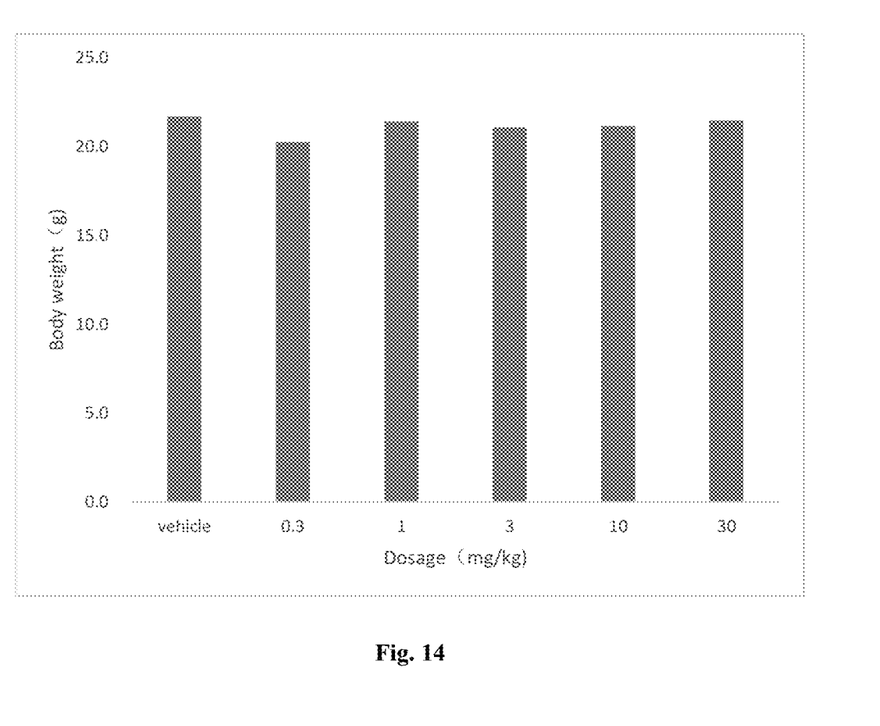
FIG. 14 is a diagram showing the effect of GBL-0603 on the body weight of normal mice in Example 4.
Figure 15:
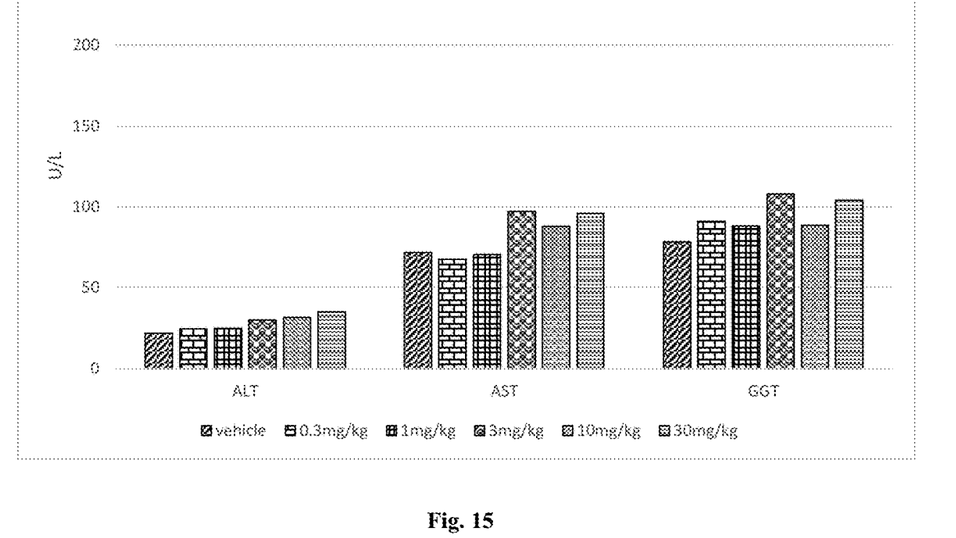
FIG. 15 is a diagram showing the effect of GBL-0603 on the liver function of normal mice in Example 4.
Figure 16:
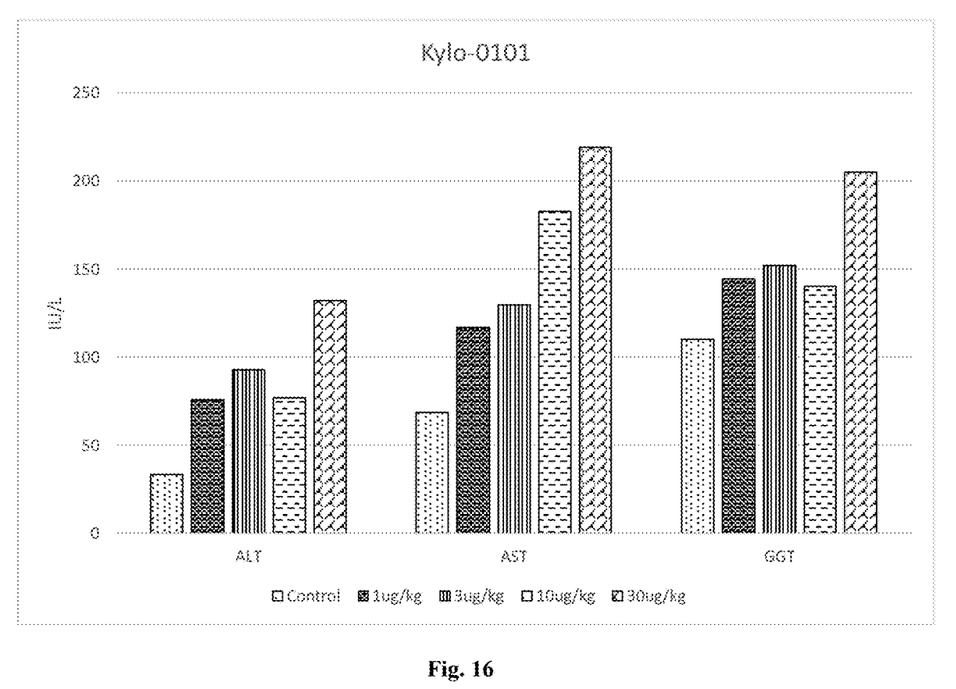
FIG. 16 is a diagram showing the effect of Kylo-0101 on the liver function of normal mice in Example 4.
Figure 17:
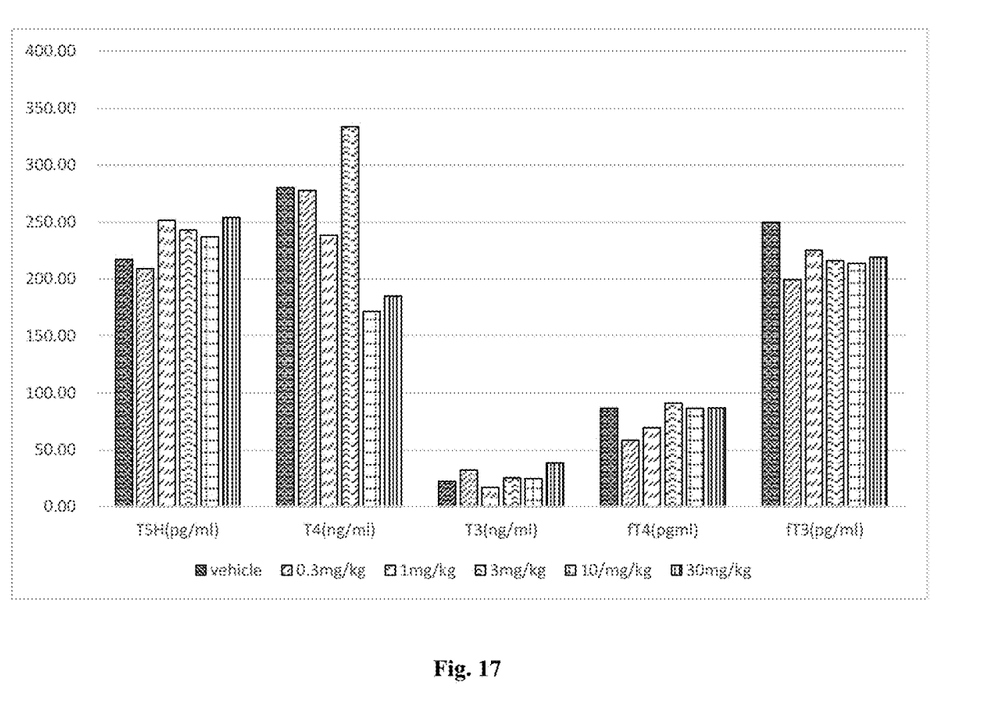
FIG. 17 is a diagram showing the effect of GBL-0603 on T3, fT3, T4, fT4 and TSH in the serum of normal mice in Example 4.

Compared with the prior art, the liver-targeting compound with the characteristics of thyroid hormone receptor agonist provided by the present invention has the following technical effects:

So far, there is no drug formally used for the treatment of NAFLD or NASH in clinic at home and abroad. The liver-targeting compound with the characteristics of thyroid hormone receptor agonist provided by the present invention has the properties of thyroid hormone β receptor as well as active liver-targeting, and overcomes the defects of exogenous thyroid hormones and early thyroid hormone β receptor agonists that have side effects on the thyroid axis, heart, muscle, bone and liver function despite their high selectivity for β1 receptors, and thus is a drug with great market potential. Compound GBL-0603 provided by the present invention can effectively reduce cholesterol (CHO), low-density lipoprotein cholesterol (LDL-C) and triglycerides (TG) in the serum of db/db mice (FIGS. 3 and 8); meanwhile, compound GBL-0603 can reduce CHO and TG in the liver of db/db mice (FIGS. 4, 9); pathological examinations showed that the fatty lesions in the liver were improved with the increase of dose (FIG. 5); no effects were showed on the heart, bone mineral density, and bone mineral content in both of db/db and normal mice (FIGS. 6, 10, 11, 12); compound GBL-0603 can significantly reduce the weight of the liver of db/db mice. In addition, compared with compound Kylo-0101 invented earlier by the inventors, the newly developed compound GBL-0603 has a milder effect on liver function (FIGS. 15, 16); no significant change was observed for each indicator of the thyroid axis at each dose of GBL-0603 (FIG. 17).

DESCRIPTION OF THE DRAWINGS

In order to make the objects, technical solutions and beneficial effects of the present invention clearer, the following description of the drawings are provided.

BEST MODE FOR CARRYING OUT THE INVENTION

The following examples illustrate some embodiments of the present disclosure, but the present invention is not limited thereto. In addition, while providing specific embodiments, the inventors anticipated application of these specific embodiments, for example, application of the compounds with specifically same or similar chemical structures in treatment of different liver-derived diseases.

Definitions

DMF refers to N,N-dimethylformamide;
HOBt refers to 1-hydroxybenzotriazole;
DIPEA refers to NN-diisopropylethylamine;
Pd/C refers to palladium on activated carbon;
TBTU refers to O-benzotiiazole-N,N,N',N'-tetramethyl-urea tetrafluoroborate;
DCM refers to dichloromethane;
NBS refers to N-bromosuccinimide;
n-BuLi refers to n-butyl lithium;
TIPSCl refers to triisopropylchlorosilane;
THF refers to tetrahydrofian;
MTBE refers to methyl tert-butyl ether;
TBAF refers to tetrabutylammonium fluoride.

Unless specified otherwise, the ratio of two substances involved in the present invention refers to the volume ratio.

Unless specified otherwise, the content involved in the present invention refers to volume percentage concentration.

Example 1: Preparation of Compound GBL-0603

1. Synthesis of Compound A
1.1 Synthesis of Compound A-c1 dlSANC-c12

-continued compound A-c1

DMF (8 mL), cbz-6-aminocaproic acid (24 mg), HOBt (21.6 mg), dISANC-c12 (84 mg) and DIPEA (53.5 mg) were added to a reaction flask in sequence. After the addition was completed, the reaction was stirred at room temperature overnight. TLC detection showed the reaction was qualified to be stopped and post-treated. The reaction was quenched with water and stood for phase separation. The aqueous phase was extracted with DCM three times, each of 20 mL. The combined organic phase was washed with saturated sodium chloride aqueous solution, dried over anhydrous sodium sulfate, concentrated, and purified by column chromatograph to obtain 72.8 mg of a white solid.

1.2 Synthesis of Compound A compound A-c1 compound A

Compound A-c1 (72.8 mg), methanol (15 mL) and Pd/C (34 mg) were added to a reaction flask in sequence, and vacuum/hydrogen replacement was performed. After the replacement. $H_2$ was introduced, and the reaction was stirred for 1.0 h at 40° C. TLC showed the reaction is qualified. The reaction is stopped and filtered to remove Pd/C. The filtrate was concentrated to obtain 47 mg of a white solid.

2. Synthesis of Compound B 2.1 Synthesis of Compound B-c1

2-isopropylphenol (30.3 mg) was weighed and dissolved in acetonitrile (10 mL), added with NBS (34.2 mg), and reacted at 35° C. for 6 h. The reaction solution was concentrated, dissolved again in petroleum ether (50 mL) and filtered to remove insolubles. The filtrate was washed with water (40 mL) and pyridine (40 mL) respectively, dried over anhydrous sodium sulfate, filtered, and rotary evaporated. The resulting residue (50.5 mg) was dissolved in acetonitrile (40 mL), added with anhydrous potassium carbonate (32.0 mg) and benzyl bromide (37.1 mg), and reacted at 40° C. for 5 h. The reaction mixture was cooled, filtered and purified by column chromatograph to give compound B-c1 (63.1 mg).

2.2 Synthesis of Compound B-c2

Compound B-c1 (63.1 mg) was weighed and dissolved in anhydrous THF (10 mL), cooled in an ice bath, added dropwise with a solution of 1.0 mol/L n-BuLi in n-hexane (5.0 mL), reacted for 3 h, added dropwise with DMF (1.5 mL), and reacted for another 3 h. The reaction was quenched with saturated ammonium chloride (5 mL), and extracted with ethyl acetate (10 mL). The organic phase was washed with pyridine (10 mL), dried over anhydrous sodium sulfate, filtered, and purified by column chromatograph to give compound B-c2 (33.4 mg).

2.3 Synthesis of Compound B-c3

4-bromo-3,5-dimethylphenol (30.8 mg) was weighed and dissolved in dichloromethane (50 mL), added with imidazole (18 mg), cooled, added dropwise with TIPSCl (25.5 mg) and reacted for 5 h. The reaction solution was diluted with dichloromethane (50 mL). The organic phase was washed with water (50 mL) and pyridine (50 mL) respectively, dried over anhydrous sodium sulfate, rotary evaporated, and purified by column chromatograph to give compound B-c3 (33.4 mg).

2.4 Synthesis of Compound B-c4

Compound B-c3 (36.1 mg) was weighed and dissolved in THF (60 mL), cooled in an ice bath, added dropwise with a solution of 1.0 mol/L n-BuLi in n-hexane (4 mL), reacted for 3 h. added dropwise with a solution of compound B-c2 (33.4 mg) in THF (5 mL), and reacted for another 3 h. The reaction was quenched with saturated ammonium chloride (20 mL), and extracted with ethyl acetate (20 mL). The organic phase was washed with pyridine (30 mL), dried over anhydrous sodium sulfate, filtered, and purified by column chromatograph to give compound B-c4 (54.3 mg).

2.5 Synthesis of Compound B compound B

Figure 1:
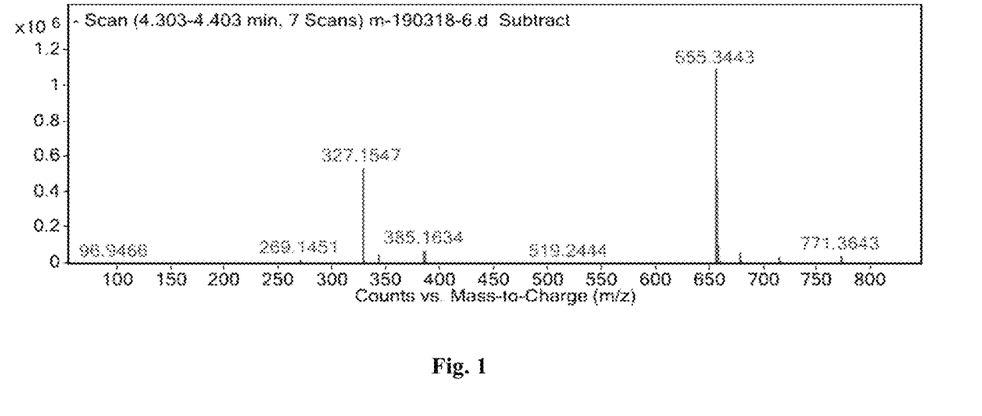
FIG. 1 is a high-resolution mass spectrum of compound B.

Compound B-c4 (54.3 mg) was weighed and dissolved in THF (50 mL), and added dropwise with a 1 mol/L TBAF solution (3 mL). TLC showed that the reaction is complete. The reaction was added with ethyl acetate (50 mL), washed with water (20 mL) and pyridine (20 mL), dried over anhydrous sodium sulfate, filtered, and rotary evaporated to give a white solid (23.3 mg). The white solid was dissolved in DMF (5 mL), cooled, added with cesium carbonate (40.4 mg) and then with benzyl bromoacetate (15.9 mg), and reacted at 40° C. for 4 h. The reaction solution was diluted with MTBE (10 mL), filtered, and added with water (20 mL). The aqueous phase was extracted with MTBE (20 mL*2), and the combined organic phase was washed with pyridine (20 mL), dried over anhydrous sodium sulfate, filtered, rotary evaporated and purified by column chromatograph. The product was dissolved in acetic acid (5 mL), added with 10% Pd/C (0.2 g) as the catalyst, hydrogenated at room temperature overnight, filtered, rotary evaporated, and purified by column chromatograph to give compound B as a light yellow solid (15 mg). The high-resolution mass spectrum of compound B is shown in FIG. 1.

3. Synthesis of GBL-0603
3.1 Synthesis of GBL-0603-c1 compound A

GBL-0603-c1

DMF (3.0 mL), compound B (15 mg), TBTU (8.47 mg) and DIPEA (20.2 mg) were added to a reaction flask in sequence and reacted for 6 h. Then compound A (47 mg) was quickly added, and the mixture was stirred at room temperature for 2 h. HPLC detected that the reaction was qualified, and the reaction was terminated.

3.2 Synthesis of GBL-0603

GBL-0603-c1

GBL-0603

Figure 2:
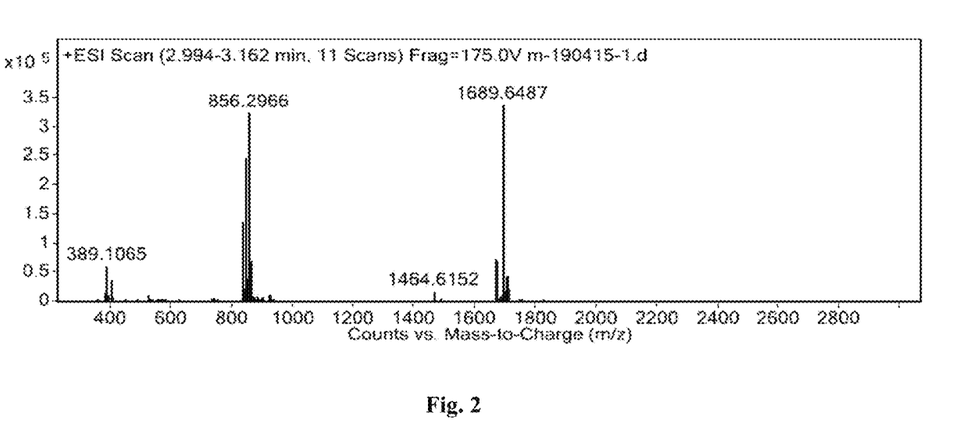
FIG. 2 is a high-resolution mass spectrum of compound GBL-0603.

After the GBL-0603-c1 reaction solution was tested to be qualified by HPLC in-process control, the pH value of the reaction solution was adjusted to 8-10 with a 1.0 mol/L ammonia solution under ice bath. After the pH value of the reaction solution was qualified, the ice bath was removed, and the reaction solution was stirred at room temperature for half an hour. HPLC in-process control analysis showed that the reaction was qualified. The pH value of the reaction solution was adjusted to 7.0 with glacial acetic acid. After the pH value of the reaction solution was qualified, it was concentrated to remove DMF in the reaction solution. The concentrated residue was dissolved in 35% acetonitrile/water, filtered, and lyophilized to give 29.47 mg of a lyophilized product. The high-resolution mass spectrum of GBL-0603 is shown in FIG. 2.

Example 2: Study on the Dose-Efficacy of GBL-0603 on Lipid Metabolism in db Mice Laboratory Animals and Breeding:

30 genetically obese model 7-week-old male mice (BKS-db) were selected. Mice need to adapt to the environment for a week before the experiment. Healthy mice were selected as test animals and reared in IVC cages at a density of 5 mice/cage, and the litter was changed twice a week. Requirements for laboratory animal room: room temperature 22-24° C., relative humidity 40 to 70%, automatic lighting, 12 h light-dark cycle (lights on at 08:00, lights off at 20:00). The laboratory animal room standards meet the national standard GB14925-2010 of the People's Republic of China.

Drug Preparation:

210 mg of GBL-0603 was accurately weighed and dissolved in 35 mL of a solvent to prepare a 6 mg/mL stock solution. Each of the dose groups was administered with the same volume by diluting the stock solution by 3, 10, 30 and 66.7 times respectively. The GBL-0603 stock solution was prepared every three days. After preparation, the stock solution was stored at 4° C. for later use.

Grouping and Dosing Schedule:

| Mice type | Quantity | Group No. | Experimental drugs | Dosage | Treatment manner |
|---|---|---|---|---|---|
| db/db control group | 6 | G1 | Blank solvent (Vehicle) | — | administered by gavage every day |

-continued

| Mice type | Quantity | Group No. | Experimental drugs | Dosage | Treatment manner |
|---|---|---|---|---|---|
| db/db administration group | 6 | G2 | GBL-0603 | 10 mg/kg | for two consecutive weeks, at 5 mL/kg |
| | 6 | G3 | | 3 mg/kg | |
| | 6 | G4 | | 1 mg/kg | |
| | 6 | G5 | | 0.45 mg/kg | |

Experimental Operation:

Before starting the experiment, blood was collected to test the total cholesterol (CHO) of the mice in each group, and the mice were weighed and randomly grouped according to body weight. The mice were weighed daily during the administration. After the last administration, the mice in each group were fasted for 6 h, and euthanized. Blood was collected from the heart, and the serum was separated to detect the levels of triglycerides (TG), total cholesterol (CHO), low-density lipoprotein cholesterol (LDL-C), ALT and AST in the serum. After blood collection, the liver was weighed, and a part of the middle lobe of the liver of the mice in each group was quick-frozen in liquid nitrogen and stored at −80° C. for later use. In addition, the middle lobe of the liver of the mice was fixed and embedded in paraffin. The heart was taken and weighed. The contents of CHO and TG in liver tissue were measured. Liver histopathological examination was performed by sectioning all mice and stained with HE, and comparing the steatosis, inflammation and ballooning of hepatocytes before and after treatment.

Example 3: Study on the Effect of Adding Sodium Caprate as an Accelerator

Animal breeding was the same as in Example 2. The grouping and dosing schedule are as follows:

| Mice type | Quantity | Group No. | Experimental drugs | Dosage | Treatment manner |
|---|---|---|---|---|---|
| db/db mice | 6 | G1 | Blank solvent (Vehicle) | — | gavage |
| | 6 | G2 | Drug A | 10 mg/kg | |
| | 6 | G3 | Drug B | 10 mg/kg | |
| | 5 | G4 | Drug C | 10 mg/kg | |

Remarks: Sodium caprate was not added in the prescription of Drug A, and was added at 20% and 75% by weight of the main drug in the prescriptions of Drugs B and C, respectively.

Experimental Operation

For G2/G3/G4, the volume of the solvent was calculated according to the weight of the drug, and then the solvent was added and vortexed repeatedly until complete dissolution for use. After the preparation, the administration was finished within one hour.

Before starting the experiment, the mice were weighed and randomly grouped according to body weight. After the last administration, the mice in each group were fasted for 6 h, and euthanized. Blood was collected from the heart, and the serum was separated to detect the levels of triglycerides (TG), total cholesterol (CHO) and low-density lipoprotein cholesterol (LDL-C) in the serum, as well as the contents of CHO and TG in the liver tissue.

Example 4: Study on the Effects of GBL-0603 and Kylo-0101 on Thyroid and Liver Enzymes in Normal Mice 66 C57BL/6J mice (half male and half female). The grouping and dosing schedule are shown in the table below:

| Mice type | Quantity | Group No. | Experimental drugs | Dosage | Treatment manner |
|---|---|---|---|---|---|
| Blank control | 6 | 1 | Blank solvent (Vehicle) | — | administered by gavage every day for two consecutive weeks |
| administration group | 6 | 2 | GBL-0603 | 30 mg/kg | |
| | 6 | 3 | | 10 mg/kg | |
| | 6 | 4 | | 3 mg/kg | |
| | 6 | 5 | | 1 mg/kg | |
| | 6 | 6 | | 0.3 mg/kg | |
| Blank control | 6 | 7 | Blank solvent (Control) | | administered by subcutaneous injection every day for two consecutive weeks |
| administration group | 6 | 8 | Kylo-0101 | 1 ug/kg | |
| | 6 | 9 | | 3 ug/kg | |
| | 6 | 10 | | 10 ug/kg | |
| | 6 | 11 | | 30 ug/kg | |

Experimental Operation

Before starting the experiment, the mice were weighed and randomly grouped according to body weight. The mice were weighed weekly during the administration. After the last administration, the mice in each group were fasted for 6 h, and euthanized. Blood was collected from the heart, and the serum was separated to detect the contents of T3, fT3, T4, fT4, and TSH in the serum; bone mineral density, body weight, liver and heart weight; liver enzymes ALT, AST and GGT, in the blank group and the GBL-0603 administration group, as well as the liver enzymes ALT. AST and GGT in the blank group and Kylo-0101 administration group.

What is claimed is:

1. A liver-targeting compound with the characteristics of thyroid hormone receptor agonist, which is a compound represented by formula (1):

formula (1)

wherein, n is an integer of 1 to 10; X is carbonyl; Y is NH or an oxygen atom.

2. The liver-targeting compound with the characteristics of thyroid hormone receptor agonist according to claim 1, which is compound GBL-0603:

GBL-0603

3. A method for preparing the liver-targeting compound with the characteristics of thyroid hormone receptor agonist according to claim 1, comprising a step of forming an ester or amide linkage between compound A and compound B:

compound A compound B wherein, n is an integer of 1 to 10; $X_1$ is —COOH; $Y_1$ is an amino group or a hydroxyl group.

4. A pharmaceutical composition for treatment and/or prevention of a disease caused by dysregulation of thyroid hormone, comprising a therapeutically effective amount of the liver-targeting compound with the characteristics of thyroid hormone receptor agonist according to claim 1, and optionally, a pharmaceutically acceptable excipient.

5. The pharmaceutical composition according to claim 4, wherein the pharmaceutically acceptable excipient includes an intestinal absorption enhancer, wherein the intestinal absorption enhancer is sodium salts of medium-chain fatty acids, cholates, cyclodextrin, cationic polymers, anionic polymers or thiolated polymers.

6. The pharmaceutical composition according to claim 5, wherein the sodium salt of medium-chain fatty acid is sodium caprate.

7. The pharmaceutical composition according to claim 4, wherein the dosage form of the pharmaceutical composition is an injection, or an oral rapid or sustained release preparation.

8. A method for treatment and/or prevention of a disease caused by dysregulation of thyroid hormone comprising administering the thyroid hormone receptor agonist according to claim 1 to a mammal in need thereof.

9. The method according to claim 8, wherein the disease is obesity, hyperlipidemia, hypercholesterolemia, diabetes, non-alcoholic fatty liver disease, alcoholic fatty liver disease, atherosclerosis, cardiovascular diseases, hypothyroidism, or thyroid cancer.

10. The method according to claim 8, wherein the disease is non-alcoholic fatty liver disease.

11. The pharmaceutical composition according to claim 6, wherein the weight ratio of the liver-targeting compound with the characteristics of thyroid hormone receptor agonist to sodium caprate is 1:0.2 to 1:0.75.

12. The liver-targeting compound according to claim 1, wherein n is an integer of 1 to 3.

13. The method according to claim 3, wherein n is an integer of 1 to 3.

* * * * *